United States Patent [19]
Lastick et al.

[11] Patent Number: 5,514,584
[45] Date of Patent: May 7, 1996

[54] **CLONING OF CELLULASE GENES FROM *ACIDOTHERMUS CELLULOLYTICUS***

[75] Inventors: Stanley M. Lastick, deceased, late of Chicago, Ill., by Harry Lastick, executor; Melvin P. Tucker, Lakewood, Colo.; Karel Grohmann, Winter Haven, Fla.

[73] Assignee: Midwest Research Institute, Kansas City, Mo.

[21] Appl. No.: 266,930

[22] Filed: Jun. 27, 1994

Related U.S. Application Data

[63] Continuation-in-part of Ser. No. 74,369, Jun. 11, 1993, abandoned.

[51] Int. Cl.$^6$ .............................. C12N 1/20; C12N 9/42; C12N 15/00; C07H 19/00
[52] U.S. Cl. .................... 435/252.3; 435/69.1; 435/209; 435/320.1; 536/22.1; 536/23.1; 536/23.2; 536/23.7
[58] Field of Search .................................. 435/69.1, 209, 435/252.3, 320.1; 536/22.1, 23.1, 23.2, 23.7

[56] References Cited

U.S. PATENT DOCUMENTS

| | | | |
|---|---|---|---|
| 4,664,471 | 8/1984 | Armentrout | 435/253 |
| 4,904,599 | 2/1990 | Ozaki | 435/252.33 |
| 5,000,000 | 3/1991 | Ingram | 435/161 |
| 5,084,385 | 1/1992 | Ashikari | 435/96 |
| 5,110,735 | 5/1992 | Tucker | 435/209 |
| 5,116,746 | 5/1992 | Bernier | 435/172.3 |

OTHER PUBLICATIONS

*Gene Cloning*, David M. Glover, pp. 110–127 (1984).
*Molecular Cloning*, Maniatis, pp. 280–281 (1982).
Honda et al., "Cloning and expression in *Escherichia coli* of a Thermoanaerobacter cellulolyticus gene coding for heat stable beta–glucanase", 25:480–483 (1987).

*Primary Examiner*—Charles L. Patterson, Jr.
*Assistant Examiner*—Hyosuk Kim
*Attorney, Agent, or Firm*—Edna M. O'Connor; Ruth Eure; Ken Richardson

[57] ABSTRACT

A process is described for moving fragments that code for cellulase activity from the genome of *A. cellulolyticus* to several plasmid vectors and the subsequent expression of active cellulase acitivty in *E. coli*.

8 Claims, 5 Drawing Sheets

FIG. 1

Restriction Maps of A. *cellulolyticus* DNA Fragments Expressing CMCase

2 kb Bam H1 fragment

3.7 kb Pvu1 fragment

CLONING OF CELLULASE GENES FROM *ACIDOTHERMUS CELLULOLYTICUS*

The United States Government has rights in this invention under Contract No. DE-AC02-83CH10093 between the United States Department of Energy and the National Renewable Energy Laboratory, a Division of the Midwest Research Institute.

CROSS-REFERENCE TO RELATED APPLICATION

This application is a continuation-in-part of our application Ser. No. 08/074,369, filed Jun. 11, 1993, now abandoned.

BACKGROUND OF THE INVENTION

1. Field of the Invention

The present invention relates generally to a process for cloning genes into a suitable host for expression of enzymes. More particularly, this invention relates to a process permitting the expression of active, recombinant *Acidothermus cellulolyticus* cellulase enzymes from *Escherichia coli*.

2. Description of the Prior Art

Although an abundant biopolymer, cellulose is unique in that it is highly crystalline, insoluble in water, and highly resistant to depolymerization. Cellulose is also an important resource that can be used to produce ethanol for use as an alternative fuel; however, before cellulose can be utilized in fermentative processes to produce ethanol, it must be hydrolyzed to glucose (possibly cellobiose, depending upon the yeast strain chosen for fermentation). One method to produce glucose from cellulose containing biomass is to use cellulase enzymes. Cellulase enzymes have been isolated from a variety of bacteria and fungi. However, most of the research on cellulase enzymes has focused on the fungal enzyme systems, and in particular, the cellulases derived from mutants of the fungal strain *Trichoderma reesei*. This is because, under certain conditions, fungal cells can export relatively large amounts of cellulase enzymes into the culture broths (Eveleigh. 1987. *Phil. Trans. R. Soc. Lond.* 321(A): 435).

Several models for *T. reesei* cellulase action have been proposed, and although differences still exist among these models, it is clear that several enzymes act synergistically in the process of hydrolyzing cellulose completely to glucose. Two types of activity, the endo-1,4-β-glucanases (EC 3.2.1.4) and the cellobiohydrolases (EC 3.2.1.91) are required to hydrolyze insoluble cellulose to produce the soluble dimer of glucose, cellobiose. A third activity, β-glucosidase (EC 3.2.1.21) mediates the hydrolysis of cellobiose to glucose.

The production of ethanol from cellulose using *T. reesei* cellulase is costly. The fungi grow relatively slowly and sugar must be sacrificed both for cell growth and for the induction of enzymes (Bernard and Helinski. 1979. *Methods Enzymol.* 68:482). In addition, cellulase from *T. reesei* is significantly inhibited by cellobiose, and to a lesser degree, by glucose. This end-product inhibition can be ameliorated by simultaneous saccharification and fermentation (SSF) (Shoemaker et al. 1981*Trends in the Biology of Fermentations for Fuels and Chemicals*, Plenum Press: New York, N.Y., pp. 89). Compatibility with SSF technology requires new cellulases to be maximally active at mildly acidic pH (i.e., pH 4 to 5).

Because the cost of producing fungal cellulase enzymes is high, alternatives to fungal production of cellulases are needed for this process to become economically feasible. The activities of some fungal and bacterial cellulases have been investigated (Beguin and Gilkes, 1987. *CRC Critical Rev. Biotechnol.* 16:129). None of the bacteria studied to date is able to export cellulases to levels as high as those produced by today's improved strains of *T. reesei*, however. Genetically engineered *Escherichia coli* have been developed which dramatically increase the amount of recombinant enzymes (in general) produced in a given period of time (Bernard et al. 1979. *Gene.* 5:59). These *E. coli* strains grow much faster than fungi, with minimal medium costs. In addition, sugar is not required for induction of the enzymes, other signals (i.e., heat shock or chemical inducers) may be used to control overproduction of the enzymes.

The production of enzymes from fungi is very slow in comparison with those from bacteria, and extremely slow in comparison with bacteria that have been genetically engineered to overproduce enzymes. For example, a mutant of the fungus that has been obtained for optimal cellulase production required a total of 4 to 5 days for the production of 5 IFPU/mL of enzyme (Shell et al. 1990. *Appl. Biochem. Biotech.* 25:287), whereas using genetically engineered *E. coli* the enzyme xylose isomerase was produced at optimal levels within less than 1 day (Lastick et al. 1986. *Biotech. Lett.* 8:1). The differences in the amounts of enzyme produced between the two procedures is equally impressive; the genetically engineered cells were able to produce xylose isomerase at a level that represented 20% of the total cellular protein due to the introduction of a temperature controlled overproduction system. Other overproduction systems are currently available that use chemical signals to initiate the overproduction of the desired enzyme.

Currently, the most efficient cellulases have been isolated from strains of the fungus, *T. reesei*. However, endoglucanases from *Thermomospora fusca* (Wilson. 1988. *Methods Enzymol.* 160:314–323), *Cellulomonas fimi* (Gilkes et al. 1984. *J. Biol. Chem.* 259:10455–10459), *Clostridium thermocellum* (Beguin et al. In *Biochemistry and Genetics of Cellulose Degradation*, Academic Press: London, UK, 1988, pp. 267–282), and other bacteria have been cloned in *E. coli* with some success. No reports of the application of recombinant technology using genes from *A. cellulolyticus* have been observed in the published literature or patents.

Highly thermostable cellulase enzymes are known to be secreted by the cellulolytic thermophile *A. cellulolyticus* gen. nov., sp. nov., a bacterium originally isolated from decaying wood in an acidic, thermal pool at Yellowstone National Park and deposited with the American Type Culture Collection (ATCC) under collection number 43068 (Mohagheghi et al. 1986. *Int. J. System. Bacteriol.* 36:435–443). *A. cellulolyticus* is a unique thermophile whose taxonomy differs from the examples of bacteria given above. The cellulase produced by this organism is known to contain several different cellulase enzymes with maximal activities at temperatures of 75° C. to 83° C. In addition, the activity of the cellulases from *A. cellulolyticus* is much less inhibited by cellobiose than that found with cellulases from *T. reesei*, an important feature for hydrolysis of cellulose in the absence of yeast or β-glucosidase. In addition, the cellulases from *A. cellulolyticus* are active over a broad pH range centered about pH 5, the pH at which yeasts are capable of fermenting cellobiose and glucose to ethanol. A novel cellulase enzyme secreted by the newly discovered microorganism is described in detail in the U.S. Pat. No. 5,110,735. In all, three distinct cellulases, the high and low molecular weight endoglucanases, and the E1 endoglucanase, have been described in this patent.

Recombinant bacterial enzymes can be used to either augment or replace the costly fungal enzymes currently used for cellulose degradation. The genes coding for *A. cellulolyticus* cellulases cloned into *E. coli*, or another industrial host, could provide an abundant source of highly active enzymes. The art of cloning *A. cellulolyticus* genes in *E. coli* or any other host organism has not been previously taught. Furthermore, is has not been previously taught that these enzymes may be useful in high temperature pretreatment of the cellulosic material prior to fermentation to ethanol.

SUMMARY OF THE INVENTION

It is an object of the present invention to provide a process for cloning genes from *A. cellulolyticus* into a suitable host for the expression of enzymes.

It is a further object of this invention to provide a process for cloning genes from *A. cellulolyticus* into a suitable host for expression of cellulase enzymes for use in cellulose degradation.

It is another object of this invention to provide a process permitting the expression of *A. cellulolyticus* cellulase enzymes from *Escherichia coli*.

It is another object of this invention to provide genetically engineered *Escherichia coli* capable of increasing the amount of recombinant enzymes produced in a given period of time. Additional objects, advantages and novel features of the invention shall be set forth in part in the description that follows and in part will become apparent to those skilled in the art upon examination of the following or may be learned by the practice of invention. The objects and the advantages of the invention may be realized and attained by means of the instrumentalities and in combinations particularly pointed out in the appended claims.

To achieve the foregoing and other objects and in accordance with the purpose of the present invention, as embodied and broadly described herein, the invention describes the process of moving DNA fragments that code for cellulase activity from the genome of *A. cellulolyticus* to several plasmid vectors and the subsequent expression of active cellulase activity in *E. coli*. The successful expression of active enzyme using *A. cellulolyticus* DNA, an organism so unlike any other that it was granted new genus and species status, was not predictable because the mechanisms governing gene expression in *A. cellulolyticus* are not well understood. The present invention provides the first demonstration of such genetic manipulation with *A. cellulolyticus* genetic material.

Genes from the cellulolytic bacterium *Acidothermus cellulolyticus* cloned into the bacterium *Escherichia coli* can be used to augment of replace enzymes currently produced from fungal sources, thus reducing the cost of fermenting biomass to ethanol. Endoglucanases known to be produced by *A. cellulolyticus* can be overproduced in *E. coli*. *E. coli* grows much faster than fungi and, by using strong, prokaryotic promoters, the overproduction of these enzymes in a bacterial host is much less costly than using slower growing fungi with their native promoters. Other advantages of the present invention will be apparent from the following detailed description and the accompanying drawings.

DESCRIPTION OF THE DRAWINGS

The accompanying drawings illustrate the proof of successful expression of active cellulase enzyme in accordance with the techniques of this invention.

FIG. 2-1 shows the restriction map of the 2 kb fragment bounded by two BamH1 sites from *A. cellulolyticus*. A restriction site for PstI and XhoI was found at about 1 kb. No sites were found within the fragment using the restriction endonucleases BglI and HpaI.

FIG. 2—2 shows the restriction map of the 3.7 kb fragment from *A. cellulolyticus* bounded by the two PvuI sites. An internal BamH1 restriction site was found.

FIG. 3 describes the activity of the cellulase expressed in *E. coli* by both plasmid constructs pMTL2-2 and pMTL4-3 versus pH. The CMC assays were conducted using 1% CMC type 7LF in constant ionic strength buffers at 65° C. A broad pH range covering 2.5 to 8.0 was used in the assays consisting of constant ionic strength McIlvaine buffers at 50 mM concentration. The pH was found to have a maxima at about 5.0 which is slightly higher than that found for the endoglucanase in U.S. Pat. No. 5,110,735 where pH of 4.0 was found to be optimal. In addition, the pH range for the endoglucanase expressed in *E. coli* with both plasmid constructs pMTL2-2 and pMTL4-3 is much broader where approximately 66% of maxima or greater is found between the pH range 2.5 and 8.0, whereas, the endoglucanase in U.S. Pat. No. 5,110,735 shows the much lower activity of approximately 25% maxima at pH 2.5 and 8.0 on the same CMC substrate in the same McIlvaine Buffers at 65° C. Because of the much broader pH range for which this endoglucanase is active the usefulness of this enzyme for industrial applications is increased. A broader pH range for activity would make the enzyme much less susceptible to inactivation in industrial processes.

FIG. 5 shows a plot of $R_f$ versus the $\log_{10}$ molecular weight of a series of known standards electrophoresed in a 12% disc SDS-PAGE gel incorporating a Tri-glycine buffer system and electrophoresed at 125 volts for 90 minutes. The dimensionless $R_f$ value was calculated by measuring from the top of the gel lane to the center of each band in that lane and dividing by the total distance the tracking dye migrated in the 12% gel under the influence of the electric field. The molecular weight of the endoglucanase expressed in *E. coli* as a result of transformation with either pMTL2-2 or pMTL4-3 was calculated by plotting the $R_f$ obtained from the 12% SDS-PAGE gel on the graph (arrow) and back calculating. The molecular weight of the endoglucanase expressed in *E. coli* by the pMTL2-2 and pMTL4-3 plasmid constructs is approximately 42,000 daltons. This value is lower than that of the high molecular weight endoglucanase disclosed in U.S. Pat. No. 5,110,735 and 81,000 daltons for the E1 endoglucanase disclosed in U.S. Pat. No. 5,275,944.

DETAILED DESCRIPTION OF THE INVENTION AND PREFERRED EMBODIMENTS

Cellulose consists of long, covalently bonded, insoluble chains of glucose which are resistant to depolymerization. However, the combined action of a complete complement of cellulase enzymes is capable of depolymerizing cellulose to cellobiose.

*A. cellulolyticus*, the source of genetic material for this invention, is an acidophilic, thermophilic microorganism capable of secreting cellulases into the medium. These cellulases have acidic pH optima, an ideal range for compatibility with yeasts, which are fully capable of fermenting the sugars produced by the action of said cellulase enzymes. The enzymes produced by *A. cellulolyticus* also show a broad temperature range from as low as 30° C. to as high as 110° C., with optima between 75° C. and 83° C. This bacterium was isolated from decaying wood samples collected in an acidic thermal pool at Yellowstone National Park. The novelty of the organism is demonstrated by acceptance in the *International Journal of Systematic Bacteriology* as a gen. nov., sp. nov., a new genus of thermophilic, acidophilic, cellulolytic bacteria (Mohagheghi et al. 1987. supra).

This invention describes the process of isolating a DNA fragment from the genome of *A. cellulolyicus* which contains a cellulase gene by cloning of genomic fragments into the EMBL-3 derivative of bacteriophage λ. A genome library was constructed using a partial Sau3AI digestion of the purified chromosomal DNA isolated from *A. cellulolyticus* and ligating size-selected (15 to 23 kb) fragments into the BamH1 cloning sites in the λ-phage EMBL-3. Recombinant phage were plated onto an *E. coli* lawn in top agar containing CMC. After overnight incubation at 37° C., plates were stained with Congo Red, followed by destaining in 1M NaCl. Clear plaques were picked as cellulose positive candidate clones. A single isolate was purified and named "SL". The cloned, large genomic DNA fragment from the recombinant phage SL was digested into smaller fragments with various restriction endonucleases and subsequently subcloned into the plasmid vectors pBR322, for amplification of the DNA, and into the plasmid vectors pDR540 or pKK223-3, for overexpression/overproduction of the enzymes encoded by the genes. Subclones expressing active cellulases were identified by screening on CMC plates as before, and the microorganisms transformed with these recombinant plasmids were selected. A 2.0 kb BamH1 fragment from the λ phage SL was positive for expression of cellulase when subcloned into the unique BamH1 site of the plasmid pDR540 (designated pMTL2-2). A 3.7 kb PvuI fragment of SL was also positive for cellulase activity when subcloned into the SmaI site of the expression plasmid, pKK223-3 (designated pMTL4-3). Liquid cultures of these *E. coli* transformants were grown to high cell density and lysed. The recombinant proteins found in these lysates, and encoded by these recombinant plasmids, displayed the properties of thermal and acid tolerance known to be associated with the native proteins isolated from the wild type organism (i.e., *A. cellulolyticus*).

EXAMPLE 1

Purification of *A. cellulolyticus* DNA

The chromosomal DNA was obtained from cultures of *A. cellulolyticus* by centrifuging the cells at 4000×g for 15 minutes. The cell pellets were frozen at −70° C., thawed, resuspended in 50 mM Tris[hydroxymethyl]aminomethane (Tris), pH 7.6, 50 mM ethylenediaminetetraacetate (EDTA), 20% sucrose, lysed with lysozyme at a concentration of 2 mg/mL followed by the addition of RNase A (0.5 g/mL) and 0.75% sodium dodecylsulfate (SDS) and incubated at 37° C. for 6 hours. The chromosomal DNA mixture was treated with protease K for 16 hours at 37° C. The protease K treated DNA was depleted of protein by treatment with phenol, phenol/chloroform/isoamyl alcohol (50:48:2 v/v) and three extractions with chloroform/isoamyl alcohol (24:1). Following centrifugation the top aqueous layer containing the chromosomal DNA was removed to new tubes and the DNA precipitated by adding 1/10 volume of 3M NaCl and two volumes of cold ethanol. Following overnight precipitation of the DNA at −20° C., the DNA was pelleted by centrifugation at 39,000×g for 30 minutes, washed with cold (−20° C.) 75% ethanol, centrifuged at 39,000×g, and air dried for 30 minutes. The *A. cellulolyticus* DNA was dissolved in TE (10 mM tris[hydroxymethyl]aminomethane, 1 mM EDTA, pH 8.0) and cesium chloride was added to a level of 37 grams per 40 mL total volume. The density of the CsCl solution was measured using the method of refractive index and found to be approximately 1.68 grams/mL of DNA solution after converting the refractive index (1.3987) to CsCl density using a standard published conversion table. Following centrifugation at 40,000 rpm in a Beckman VTi 50 rotor for 62.5 hours the CsCl gradient was fractionated into 0.5 mL aliquots from the top of the tube to the bottom. The purified chromosomal DNA was found near the center of the CsCl gradient by monitoring the ultraviolet absorbance at 254 nm as the centrifugation tubes were being fractionated. The chromosomal DNA fractions were pooled and dialyzed against TE overnight and recentrifuged using CsCl at a starting density of 1.68 g/mL for 44 hours at 40,000 rpm in an Beckman VTi50 rotor. The second CsCl gradient was fractionated and the *A. cellulolyticus* DNA found near the middle of the gradient was pooled and exhaustively dialyzed against TE buffer. The crude preparations of chromosomal DNA were purified by centrifuging in CsCl gradients without the addition of ethidium bromide, a reagent known to attack DNA in the presence of fluorescent lighting and especially ultraviolet light used in the standard procedures to visualize the isopycnically banded DNA. The method used here to isolate chromosomal DNA from *A. cellulolyticus* although more troublesome, does not expose the DNA to ultraviolet light with ethidium bromide present as the exposure to UV occurs only for limited times within the micro (15 microliter) flow cell during monitoring of the fractionation of the cesium chloride gradient and no ethidium bromide is present.

EXAMPLE 2

Isolation of Sized DNA Fragments

Aliquots of the CsCl purified and dialyzed chromosomal DNA were subjected to restriction endonuclease digestion with varying amounts of restriction enzymes. The most preferred amount of Sau3AI added appeared to be 0.0625 units of enzyme per microgram of purified DNA in order to give a pseudorandom partial digestion. Other restriction enzymes used included EcoR1. The partially digested chromosomal DNA was loaded onto an 1.0% agarose gel in 0.5×TBE buffer and electrophoresed until well separated using a pulsed reverse field technique comprising a 450 millisecond forward electrophoresis pulse followed by an 150 millisecond reverse pulse. The forward and reverse pulse lengths were increased steadily in a ramped manner at the rate of 0.6 per hour for the entire electrophoresis time of 7.5 hours. Again the DNA was electrophoresed without the presence of ethidium bromide to lower the possibility of damage to the DNA. The partially digested DNA, in the size range from 15 kilobases to 23 kilobases in length when compared to standard DNA fragments run along side in the same gel, was excised from the gel while remaining trapped within the agarose matrix and vortexed vigorously in the presence of phenol for one minute, frozen at −20° C. for 1 hour and at 31 70° C. overnight. The frozen gel slices were centrifuged at 15,000×g for 15 minutes to separate the phenol and agarose gel phase from the aqueous DNA containing phase, which was then precipitated at −20° C. following the addition of 1/10 volume of 3M NaCl and two volumes of cold (−20° C.) ethanol. The precipitated partially digested and sized chromosomal DNA was centrifuged to pellet the DNA, washed with cold 75% ethanol, air dried for 30 minutes, and redissolved in TE buffer.

EXAMPLE 3

Selection of Phage Isolate Carrying *A. cellulolyticus* Cellulase DNA

Aliquots of the redissolved DNA were ligated to the BamH1 digested and dephosphorylated arms of the λ phage EMBL-3 overnight at 12.5° C. The recombinant phage DNA was packaged into λ precursor phage head proteins using the Packagene® kit from Promega. Recombinant phage containing cellulase genes were selected by plating the packaged phage with the *E. coli* strain NM 359(supF, hsdR($r_k^-$ $m_k^+$, (P2) in an overlay of 0.7% agar, 10 mM MgSO$_4$, 0.5% CMC (Sigma low viscosity). The overlays with the lawn of bacteria were quickly poured on top of agar (1.5%) containing 5 g Bacto tryptone, 2.5 g Bacto yeast extract and 5 g NaCl per liter. The buffer MES (2-(N-morpholino)ethanesulfonic acid) at a concentration of 50 mM and pH of 6.0 was used to buffer the overlayed transfected *E. coli* lawn. This was found to be necessary because rapidly growing *E. coli* colonies and lawns in aerobic growths on plates was found to change the pH of the plate. Numerous other buffers were tried including PIPES (Piperazine-N,N'-bis[2-ethanesulfonicacid]), Bis-Tris(bis[2-hydroxyethyl]imino-tris[hydroxymethyl]methane), citrate, and phosphate. MES was found to work best at keeping the pH low enough to be near the optimal level for the cellulase enzymes, yet high enough to allow for growth of the recombinant *E. coli* and yet not unduly inhibit the cellulase enzymes. Without the addition of MES at pH 6.0 it would have been very difficult to detect the cellulase activity. The plates containing the lawn of *E. coli* with interspersed recombinant phage plaques were incubated overnight at 37° C. The plates were stained with Congo red (1 mM) for 30 minutes with gentle shaking, and then destained with several washes of 1M NaCl.

A plaque showing a clear halo, i.e., free of red stain, indicating hydrolysis of the CMC, i.e., endoglucanase activity, was excised from the top overlay using glass pasteur pipets and soaked in SM buffer (50 mM Tris-Cl, 100 mM NaCl, 8 mM MgSO$_4$, 0.01% gelatin, pH 7.5) overnight at 4° C. to allow for diffusion of the recombinant phage from the agar plug. This isolate, called SL, was then titered and diluted. Samples of the isolate were tested by spotting 5 µL onto plates overlaid with *E. coli* cells and CMC as described above. Positive isolates were then purified by re-plating at a dilution that produced 20 to 30 plaques per plate, without staining. Seven plaques from SL were then re-tested by spot tests and one positive isolate of each of the seven was used to prepare large-scale lysates.

EXAMPLE 4

Preparation of *A. cellulolyticus* DNA from Phage

Larger-scale lysates were produced by plating SL plaques on LB medium plates supplemented with 0.2% glucose, 0.075 mM CaCl$_2$, 4 µM FeCl$_2$, and 2 mM MgSO$_4$. The plates were incubated for 6–8 hours, until the plaques became nearly confluent, and 1 mL SM buffer was added to each plate and the phage were allowed to diffuse into the buffer overnight at 4° C. The phage extracts were centrifuged to remove debris and the supernatants, containing about $5\times10^9$ pfu/mL, were used to isolate the DNA. The phage were concentrated using the immuno-adsorbant LambdaSorb® (Promega), as recommended by the supplier. An alternate method involving the pelleting of the phage through step gradients of 5% and 40% glycerol in an ultracentrifuge at 80,000×g for 1 hour gave identical results. The purified phage were treated with RNase A (25 µg/L) and DNaseI (1 µg/L) at 30° C. for 30 minutes, and the DNA was extracted with TE saturated phenol, chloroform, isopropanol, and ethanol precipitated, dried and stored in TE buffer at 4° C.

EXAMPLE 5

Ligation of *A. cellulolyticus* DNA Fragment into Plasmid Vectors

Phage systems lack overproduction capabilities, and because of the difficulty of obtaining large amounts of recombinant enzymes from phage lysate methodologies, subcloning of DNA fragments obtained from the SL phage isolate into overexpression vectors was carried out.

The purified phage DNA was digested with several restriction endonuclease enzymes including BamH1, EcoR1, and PvuI. The digestions carried out with each enzyme were electrophoresed using the pulsed reverse field method in 1.0% agarose gels with 0.5×TBE buffer at 300 volts with 150 msec forward pulse, 50 msec reverse pulse, with pulse lengths increasing at the rate of 0.6 hr$^{-1}$. EcoR1 digestions yielded 1.9 kb, 2.4 kb, and 4 kb DNA fragments, BamH1 digestions yielded a 2.0 kb fragment, and PvuI digestions yielded 1.7 kb, 2.0 kb, 3.0 kb, and 3.7 kb fragments. Each of the bands containing fragments of one particular size of digested DNA were excised out of the gel. The agarose gel did not contain ethidium bromide for reasons stated above. The gel slices were vortexed vigorously in the presence of TE saturated phenol, and frozen at −20° C. for 1 hr followed by freezing at −70° C. overnight. The frozen suspensions were centrifuged at 15,000×g for 15 minutes and the aqueous supernatants containing the DNA were extracted with TEN saturated phenol, and chloroform/isoamyl alcohol (24:1 v/v) and ethanol precipitated overnight at −20° C. The pelleted DNA fragments were centrifuged at 15,000×g for 15 minutes, washed with 70% ethanol, dried and redissolved in TE buffer. In some cases, the purified DNA fragments were blunt-ended using the enzyme $T_4$ DNA polymerase incubated at 37° C. in the presence of dNTPs.

Aliquots of the restriction endonuclease fragments were ligated to the plasmid vectors pBR322, pDR540, and pKK223-3. Plasmid vectors pDR540 and pKK223-3 are noteworthy because they carry tac promotors upstream of the cloning sites. These promotors are inducible by addition of IPTG (isopropyl-β-D-thiogalactopyranoside). Prior to the ligation, the plasmid vectors were cut by the appropriate restriction endonuclease. The restriction endonucleases used being BamH1, EcoR1, Pvu1 or Sma1, followed dephosphorylation with calf intestinal alkaline phosphatase. The dephosphorylation was necessary to decrease the background of non-recombinant transformed colonies.

EXAMPLE 6

Transformation of *E. coli* with *A. cellulolyticus* DNA

The *Escherichia coli* host strains used for transformation were HB101 [proA2, ara14, lacY1, galK2, xyl5, mtlT1, recA13, rpsL20(str), supE44, hsdS20 (rb–, mb–)λ–] and DH5α [F–, ϕ80dlacZΔM15, Δ(lacZYA-argF) U169, deoR, recA1, endA1, jsdR17 ($r_K^-$, $m_K^+$), supE44, λ–, thi-1, gyrA96, relA1]. The cells were made competent using standard methods of calcium chloride, or the rubidium chloride method. The cells were transformed with the recombinant plasmid vectors by incubating the competent cells on ice in the presence of the plasmid for 30 minutes to 1 hour, heat shocking the cells at 37° C. or 42° C. for 30 seconds to 2 minutes, incubating the cells on ice an additional 2 minutes, adding SOC medium and incubating the cells at 37° C. for 1 hour to allow expression of the particular antibiotic resistance gene.

In the case of the 2.0 kb fragment inserted into the BamH1 site of pBR322, the tetracycline resistance gene is inactivated by the foreign DNA; however, the ampicillin resistance gene is still intact, and recombinant colonies can be selected using nutrient agar plates containing 5 g Bacto tryprone, 2.5 g Bacto yeast extract, and 5 g NaCl supplemented with ampicillin at the level of 50 to 100 µg/mL. When the 3.7 kb fragment from the Pvu1 digest of SL is inserted into the Pvu1 site within pBR322, the ampicillin resistance gene is inactivated; however, selection is made using the intact tetracycline resistance gene and tetracycline supplemented (15 µg/mL) nutrient agar plates. The selection of recombinant colonies carrying the transformed plasmids pDR540 and pKK223-3 were made possible using the intact ampicillin resistance gene and selection on ampicillin supplemented nutrient agar plates. It was found necessary to supplement the nutrient agar plates with 50mMMES, pH 6.0, in order to detect cellulase activity.

Cellulase activity within the cells transformed with the recombinant plasmids was detected by using the fluorescent substrate 4-methylumbelliferyl-β-D-cellobiopyranoside (4-MUC) at the level of 0.5 mM or CMC supplemented in the nutrient agar plates at the level of 0.5%. Congo red (1 mg/mL) was used to detect cellulase activity by staining the unhydrolyzed CMC. Colonies possessing cellulase activity produced clearing zones that were not stained by Congo red. Positive colonies expressing cellulase activity were substreaked additional times until pure and tested using nutrient agar plates supplemented with the appropriate antibiotic and 4-MUC or CMC.

Recombinant cells transformed with plasmids constructed from pKK223-3 digested with EcoR1, ligated to purified 1.9 kb, 2.4 kb, and 4 kb EcoR1 digested fragments of SL, each failed to express cellulase activity. Recombinant cells transformed with plasmids constructed from pBR322 digested with Pvu1, ligated to purified 1.7 kb, 2.0 kb and 3.0 kb Pvu1 digested fragments of SL, also each failed to express cellulase activity. Recombinant cells transformed with plasmids constructed from pDR540 digested with BamH1, ligated to a 2.0 kb BamH1 digested fragment from SL, showed cellulase activity; and recombinant cells transformed with plasmids constructed from pKK223-3 digested with Sma1, ligated to a 3.7 kb Pvu1 digested ($T_4$ DNA polymerase treated) fragment from SL, also showed positive cellulase activity (i.e., CMC clearing zones). Cultures of *E. coli* DH5α transformed with the pDR540:2.0 kb and pKK223-3:3.7 kb constructions are referred to here as DH5α(pMTL2-2) and DH5α(pMTL4-3).

EXAMPLE 7

Demonstration of Successful Expression of *A. cellulolyticus* Cellulase Enzymes in *E. coli*

Non-denaturing discontinuous polyacrylamide gel electrophoresis (PAGE) was performed using aliquots of the lysates prepared from DH5α(pMTL2-2), as well as samples from the supernatant of *A. cellulolyticus* grown on cellulose, and two purified *A. cellulolyticus* cellulase enzymes, the high and low molecular weight endoglucanases.

The 1.5 mm thick gels consisted of 7.5% acrylamide monomer concentrations with 5% crosslinking agent (N,N'-methylene-bis-acrylamide). The resolving gel buffer consisted of 236.8 mM Tris, 72.3 mM HCl, pH 8.48. The stacking gel consisted of 3.125% total monomer with 20% crosslinking in 39.5 mM Tris, 64 mM HCL buffer at pH 6.9. A constant 30 mA per gel was used to carry out the electrophoresis. Following electrophoresis, the gels were overlayed on baking dishes containing 200 mL hardened 1.5% agar, 50 mM acetate buffer, pH 5.0, and 0.5% CMC (low viscosity; Sigma Chemical Co.) according to the method of obtaining a zymogram. The baking dishes and gels were incubated at 55° C. for 2 hr and stained with Congo red (1 mg/mL) for 30 minutes followed by destaining twice with 1M NaCl for 30 minutes each.

Figure 1:
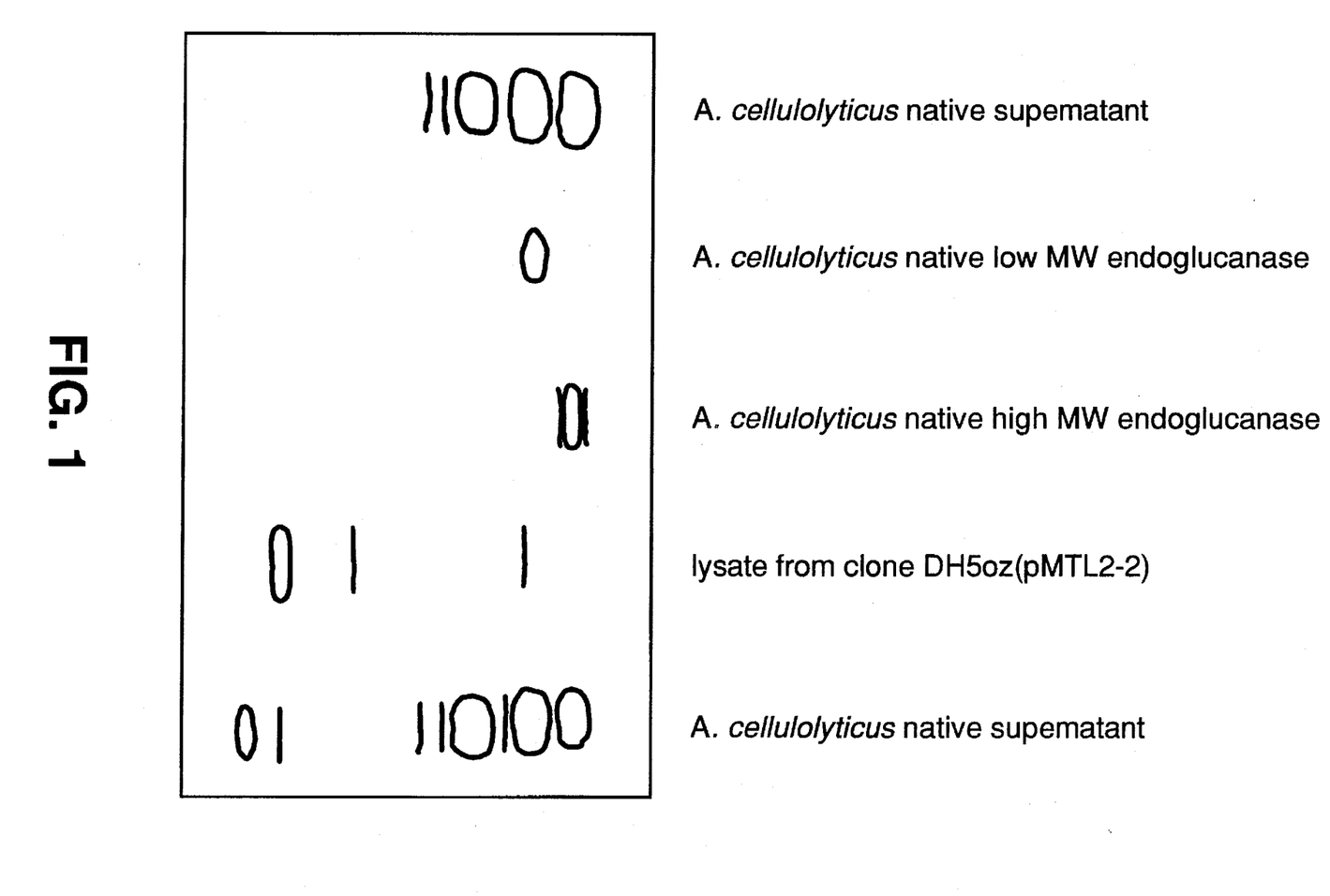
FIG. 1 shows the native protein polyacrylamide gel electrophoresis of two, purified *A. cellulolyticus* endoglucanases, *A. cellulolyticus* crude growth supernatant, and the lysates obtained from DH5α (pMTL2-2) (i.e., the *E. coli* transformed with the vector plasmids pDR540:2.0 kb). This drawing is a direct tracing of the original gel; faint bands shown as single lines). The gel shows activity of the protein bands by the zymogram method (Teather and Wood. 1982. *Appl. Environ. Microbiol.* 43:777), where endoglucanase activity is demonstrated by preferential binding of Congo Red dye to carboxymethylcellulose (CMC) incorporated into an agar gel upon which the electrophoresed gel is incubated. Activity is shown by cleared areas on the CMC-agar overlay gel following flooding the gel with Congo Red and destaining with sodium chloride solution.

The clearing zones around bands in each lane indicate cellulase activity (see FIG. 1). Minor bands visible in some lanes (i.e., drawn as single lines) probably indicate low level protease degradation of the *A. cellulolyticus* cellulases. The primary recombinant cellulase band (i.e., from pMTL2-2:2.0 kb) was found to comigrate in the native PAGE with a very minor band observed in native *A. cellulolyticus* supernatant. This recombinant cellulase does not appear similar by this criterion to either the purified *A. cellulolyticus* high and low molecular weight endoglucanases also shown in FIG. 1.

EXAMPLE 8

Demonstration of the Overproduction of *A. cellulolyticus* Cellulase in *E. coli*

Cultures (200 mL) of the transformed cells of DH5α(pMTL4-3) were grown overnight in LB medium (10 gm Bacto tryptone, 5 g Bacto yeast extract, 5 g NaCl per liter) at 37° C., and the cells harvested by centrifugation at 4,000×g for 15 minutes. In the case of the plasmids used for overproduction, the liquid culture medium was supplemented with 1 mMIPTG. Identical experiments were carried out at the same time using cells transformed with the recombinant overproduction plasmids; however, the liquid medium lacked added IPTG. The purpose was to test for chemical control of overproduction of the cellulases.

Following harvesting of the cells, the pelleted cells were washed once with 50 mM acetate buffer at pH 5.0, and the cell pellets lysed in 3 mL of 50 mM acetate buffer by passage through a French pressure press operated at 20,000 psi and a flow rate of about 1 drop every 20 seconds. Usually three passages of the cell lysate through the French press was required to get complete lysis of the recombinant cells as determined by microscopic examination. The cell debris was centrifuged out at 40,000×g for 30 minutes at 4° C., and the supernatants assayed for cellulase activity using p-nitrophenyl-β-D-cellobiopyranoside (pNPCB), a known substrate for *A. cellulolyticus* endoglucanases. The assays consisted of adding 1 mL of a 1 mg/mL solution of pNPCB or pNPG in 50 mM acetate buffer at pH 5.0. The assay mixtures were incubated at 65° C. for 1 hour and then quenched by the addition of 2 mL of 2M $Na_2CO_3$.

The culture grown in the presence of IPTG showed enhanced production of activity on pNPCB relative to the culture grown in the absence of IPTG (TABLE 1). This example shows the successful application of tac promotor regulation and subsequent overexpression of an *A. cellulolyticus* gene in *E. coli*. This example also shows the thermostability of the recombinant cellulases produced by the transformants, i.e., activity was measurable after a 1-hour incubation at 65° C.

TABLE 1

The increase in endoglucanase activity from transformant DH5α (pMTL4-3) grown both in the presence and absence of the tac promotor inducer, IPTG.

|  | Growth with IPTG | Growth w/o IPTG |
|---|---|---|
| $OD_{600\ nm}$ of culture at harvest | 0.674 | 0.707 |
| Cell mass wet weight | 2.28 g | 2.39 |
| Volume of cell lysate | 5.3 mL | 5.5 mL |
| pNPCB activity (OD410) | 1.681 | 1.261 |
| pNPCB activity (units) | 2.16 | 1.62 |
| specific activity (units/g cells) | 0.947 | 0.678 | units pNPCB activity = nmol/min at 65° C.

The foregoing is considered as illustrative only of the principles of the invention. Further, because numerous modifications and changes will readily occur to those skilled in the art, it is not desired to limit the invention to the exact construction and operation shown and described, and accordingly all suitable modifications and equivalents may be restored to falling within the scope of the invention as defined by the claims which follow.

Figure 2:
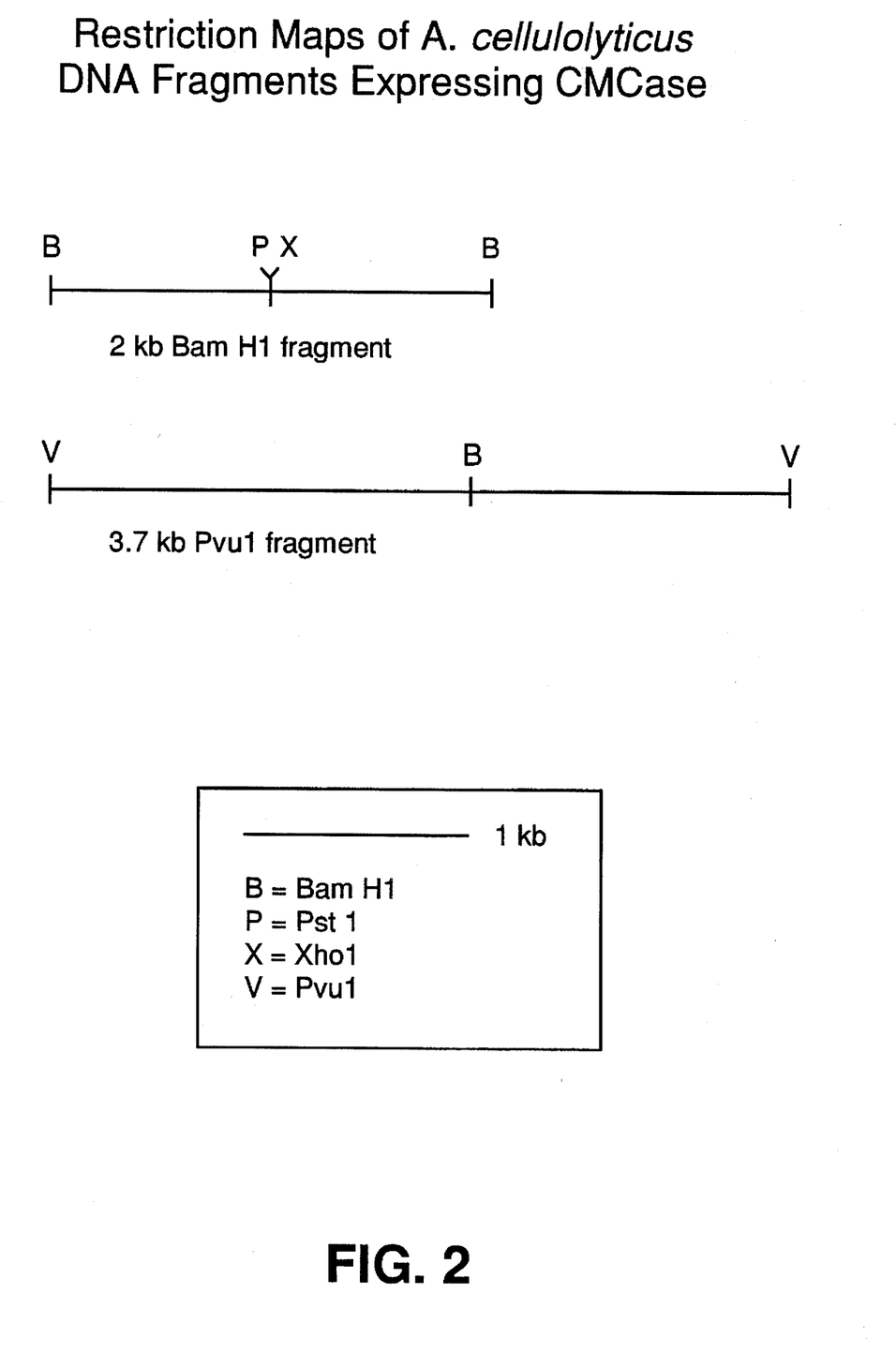
Figure 3:
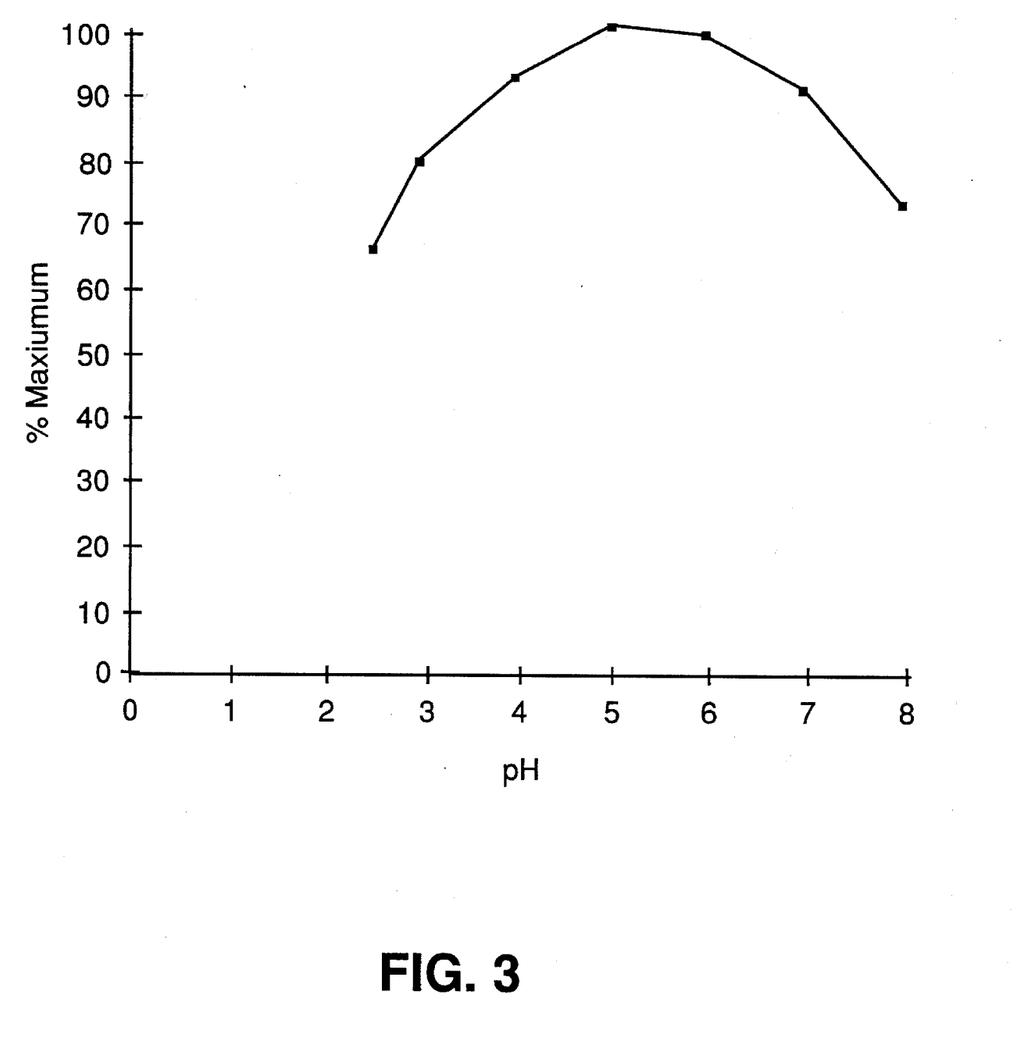
Figure 4:
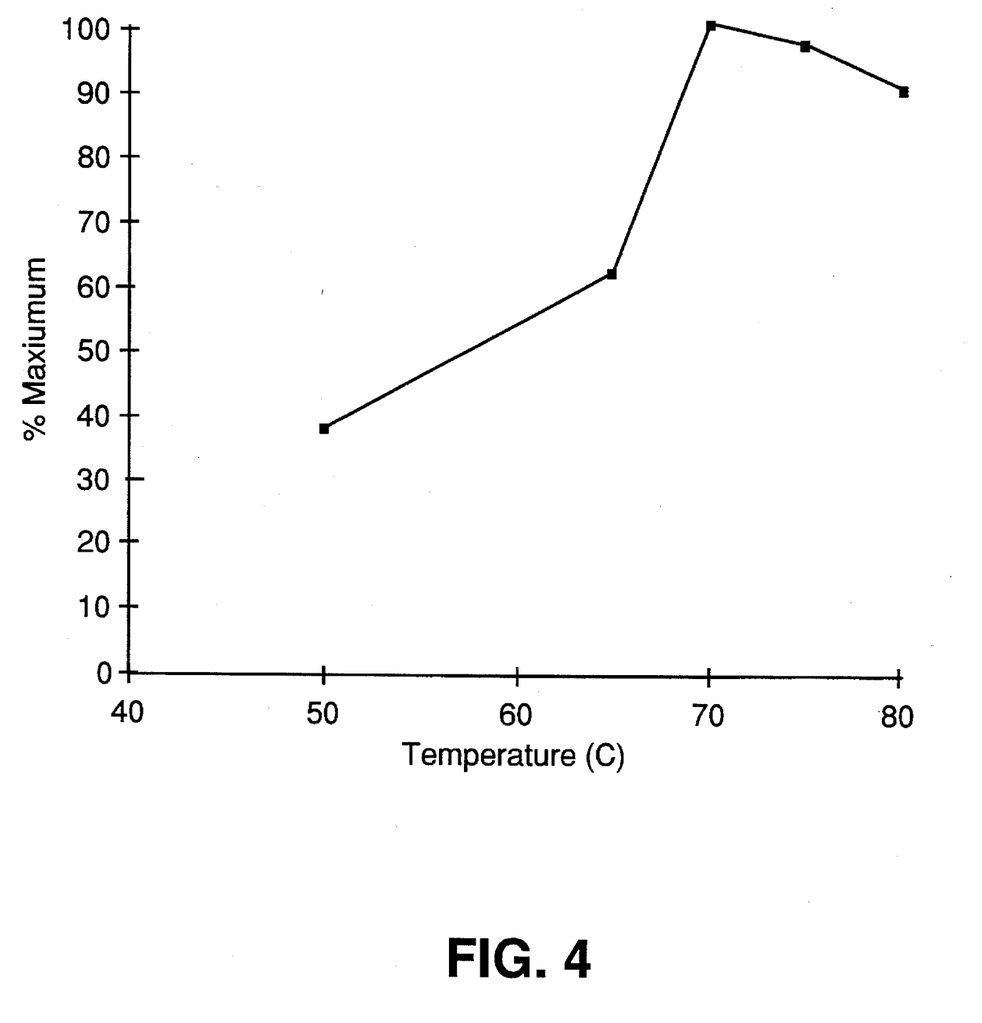
FIG. 4 describes the cellulase activity expressed in *E. coli* by both plasmid constructs pMT2-2 and pMTL4-3 as a function of temperature. The temperature optima is about 70° C. for this cellulase versus 83° C. for the endoglucanase in U.S. Pat. No. 5,110,735 and 85° C. for the E1 endoglucanase in U.S. Pat. No. 5,275,944. Although the temperature optima is lower, approximately 90% of maximal activity remains at 80° C. making this endoglucanase useful in higher temperature industrial applications.
Figure 5:
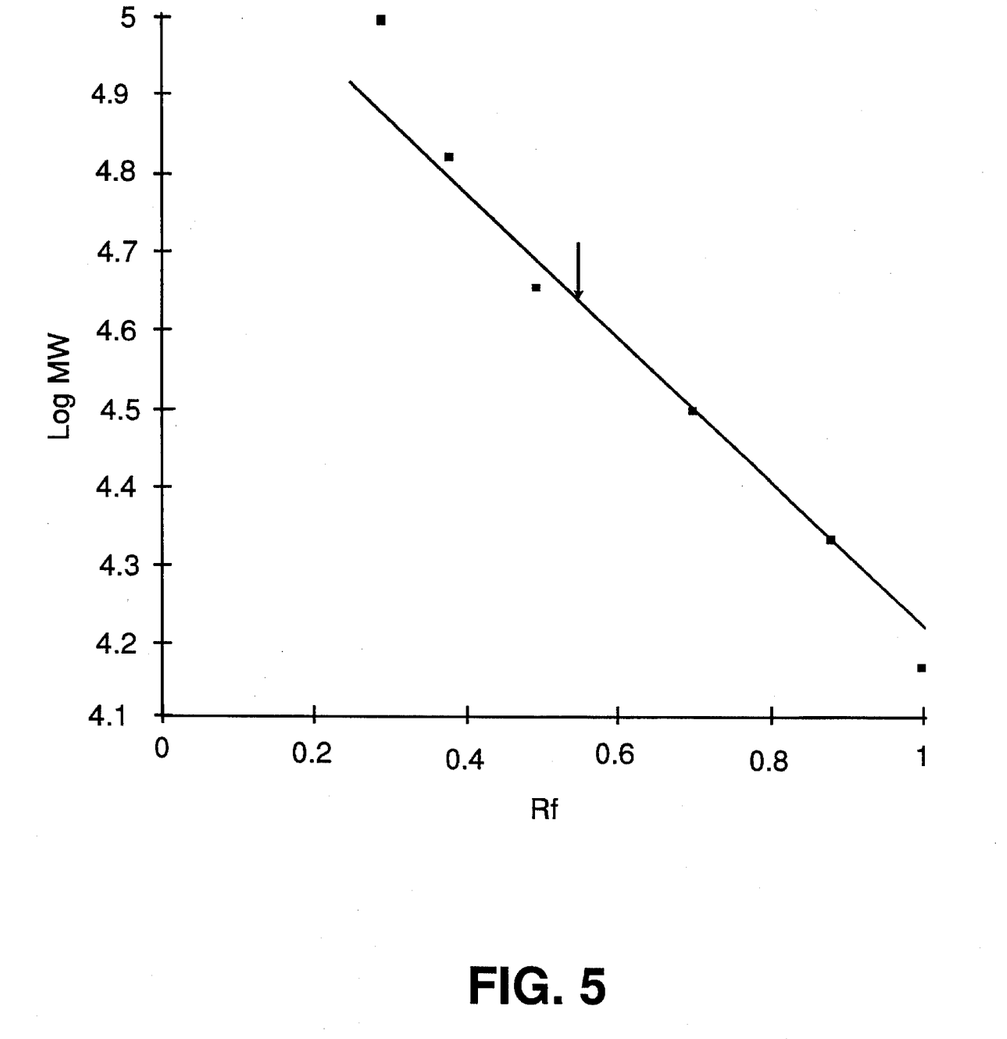

The embodiments of the invention in which an exclusive property or privilege is claimed are defined as follows:

1. A DNA fragment coding for cellulase enzymes which comprises about 2.0 kilobase pairs and is described by a restriction map shown in FIG. 2-1; wherein said DNA fragment is isolated from *Acidothermus cellulolyticus*.

2. A DNA fragment coding for cellulase enzymes which comprises about 3.7 kilobase pairs and is described by a restriction map shown in FIG. 2—2; wherein said DNA fragment is isolated from *Acidothermus cellulolyticus*.

3. A recombinant plasmid comprising a DNA fragment of claim 1.

4. A recombinant plasmid comprising a DNA fragment of claim 2.

5. A recombinant plasmid comprising a DNA fragment of claim 1 coding for cellulase enzymes and including additional DNA element which enables overproduction of said cellulase enzymes.

6. A recombinant plasmid comprising a DNA fragment of claim 2 coding for cellulase enzymes and including additional DNA element which enables overproduction of said cellulase enzymes.

7. A transformed microorganism carrying a recombinant plasmid comprising a DNA fragment coding for cellulase enzymes, wherein said DNA fragment comprises approximately 2.0 kilobase pairs which is described by the restriction map shown in FIG. 2-1, wherein said DNA fragment is isolated from *Acidothermus cellulolyticus*, wherein said transformed microorganisms comprises *E. coli* bacterium strain DH5α or strain HB101.

8. A transformed microorganism carrying a recombinant plasmid comprising a DNA fragment coding for cellulase enzymes, wherein said DNA fragment comprises approximately 3.7 kilobase pairs which is described by the restriction map shown in FIG. 2—2, wherein said DNA fragment is isolated from *Acidothermus cellulolyticus*, wherein said transformed microorganism comprises *E. coli* bacterium strain DH5α.

* * * * *